United States Patent
Dagle et al.

(10) Patent No.: US 10,538,464 B1
(45) Date of Patent: Jan. 21, 2020

(54) PROCESS FOR ENHANCED PRODUCTION OF DESIRED HYDROCARBONS FROM BIOLOGICALLY-DERIVED COMPOUNDS AND BIO-OILS CONTAINING CYCLIC COMPOUNDS BY OPENING OF AROMATICS AND NAPHTHENIC RING-CONTAINING COMPOUNDS

(71) Applicant: BATTELLE MEMORIAL INSTITUTE, Richland, WA (US)

(72) Inventors: Vanessa Dagle, Richland, WA (US); Karl O. Albrecht, Richland, WA (US); Robert A. Dagle, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 16/165,198

(22) Filed: Oct. 19, 2018

(51) Int. Cl.
*C07C 4/06* (2006.01)
*C10G 11/04* (2006.01)
*B01J 19/24* (2006.01)

(52) U.S. Cl.
CPC ............. *C07C 4/06* (2013.01); *B01J 19/245* (2013.01); *C10G 11/04* (2013.01); *C07C 2521/04* (2013.01); *C07C 2523/46* (2013.01); *C07C 2529/74* (2013.01); *C10G 2300/1014* (2013.01)

(58) Field of Classification Search
CPC ............. C07C 4/06; C10G 11/04; B01J 19/24
See application file for complete search history.

(56) References Cited

U.S. PATENT DOCUMENTS 8,053,615 B2* 11/2011 Cortright ................. C10G 3/45
585/240

OTHER PUBLICATIONS

McVicker, G. B., et al., Selective Ring Opening of Naphthenic Molecules, Journal of Catalysis, 210, 2002, 137-148.
Santikunaportn, M., et al, Ring contraction and selective ring opening of naphthenic molecules for octane number improvement, Applied Catalysis A: General, 325, 2007, 175-187.

* cited by examiner

*Primary Examiner* — Youngsul Jeong
(74) *Attorney, Agent, or Firm* — Derek H. Maughan

(57) ABSTRACT

A system and process for processing biologically-derived compounds or a complex bio-oil by converting cyclic compounds in a complex bio-oil or biologically-derived compounds to desired materials such as high molecular weight paraffins with minimal carbon loss by using a ring-contraction catalyst to selectively produce $C_5$ ring containing compounds; and then reacting the $C_5$ ring containing compounds with a $C_5$ ring opening catalyst in a second reactor to minimize carbon loss via cracking reactions.

11 Claims, 2 Drawing Sheets

---

Step 1

Convert C-6 compounds or mixtures containing C-6 compounds to C-5 compounds or mixtures containing C-5 compounds Step 2

Convert C5 compounds or mixtures containing C-5 compounds to desired material

Step 1
Convert C-6 compounds or mixtures containing C-6 compounds to C-5 compounds or mixtures containing C-5 compounds

Step 2
Convert C5 compounds or mixtures containing C-5 compounds
to desired material

Figure 2

PROCESS FOR ENHANCED PRODUCTION OF DESIRED HYDROCARBONS FROM BIOLOGICALLY-DERIVED COMPOUNDS AND BIO-OILS CONTAINING CYCLIC COMPOUNDS BY OPENING OF AROMATICS AND NAPHTHENIC RING-CONTAINING COMPOUNDS

STATEMENT AS TO RIGHTS TO DISCLOSURES MADE UNDER FEDERALLY-SPONSORED RESEARCH AND DEVELOPMENT

This disclosure was made with Government support under Contract DE-AC0576RL01830 awarded by the U.S. Department of Energy. The Government has certain rights in the invention.

BACKGROUND OF THE DISCLOSURE

The consumption of diesel and jet fuels in the United States is estimated to range from between 20 and around 50 billion gallons per year. While the integration of biofuels into this market has been growing, currently biodiesel represents less than 1% of the total U.S. diesel market and nearly all aviation fuels are currently derived from fossil fuel sources. As with many forms of fossil fuels, a desire exists to replace the use of these finite and non-renewable resources with renewable resources such as those based upon biomass. Biofuel based diesel and jet fuels are not only in accordance with the U.S. government's vision for future fuels but also encouraged by the American airline industry.

Bio-fuels can come from a variety of sources including bio-oils derived from various based sources. However, most bio-oils are complex microemulsions of aqueous and non-aqueous phases containing hundreds of different organic and inorganic compounds. Oxygenated hydrocarbons found in bio-oils can include esters, acids, aldehydes, alcohols, ketones, sugars, and various phenol derivatives. These reactive species in bio-oils complicate storage, transportation, and downstream processing because secondary reactions can cause condensation and polymerization which increase the viscosity of the bio-oil and form problematic solids. This in turn leads to other problems including coking which can render catalysts intended to treat these materials ineffective. Bio-oils can also contain organic acids such as acetic acid and formic acid as well as phenolics that can cause corrosion and damage the infrastructure of conventional processing systems. In view of the types of complexities and problems various methods are sought to remove these reactive functionalities to improve bio-oil stability.

Stabilization of bio-oils by hydrogenation is typically performed using pressurized hydrogen ($H_2$) at elevated temperatures. However, bio-oils lack thermal stability and, upon break down, compounds in bio-oils form coke which block catalyst sites and plugs reactors during treatment at elevated temperatures. Among the plugging items and undesired materials that arise in bio-oil preprocessing are cyclic hydrocarbons. Bio-fuels obtained from typical direct liquefaction routes such as fast pyrolysis, catalytic fast pyrolysis, and hydrothermal liquefaction typically create a generally high number of cyclic carbon chains, including aromatics like alkylbenzenes and cycloparaffins such as alkylcyclohexanes. Converting these types of products into fuel-type chemicals can make the insertion of such a treated bio-oil into a standard fuel delivery or refining system is one potential way of increasing the use and application of complex bio-oils and enhances the likelihood of their eventual adaptation into the diesel and jet markets. The present disclosure provides significant advance in this field by providing a path toward such a conversion.

SUMMARY

A system and process are described for processing biologically-derived cyclic compounds and/or biomass-derived mixtures such as a complex bio-oils and containing cyclic compounds by converting the cyclic compounds into desired materials such as high molecular weight materials such as paraffins with minimal carbon loss through cracking reactions. This work reported here is the first known extension of the ring-opening process to both biologically-derived compounds and bio-oils. In one example the method includes the steps of reacting a precursor containing cyclic compounds in a first a reactor with a ring-contraction catalyst to selectively produce C-5 ring containing compounds; and then reacting the C-5 ring containing compounds with a C-5 ring opening catalyst in a second reactor to yield a high molecular weight material. The first reactor may operates under a first set of operating conditions and the second reactor may operate under a second set of conditions. The first and second sets of conditions may be different. In some embodiments the ring contraction catalyst is an acid catalyst containing Pt. In other instances the ring contraction catalyst is an acid catalyst containing Pd. The C-5 ring opening catalyst could be a metal catalyst, such as Ir.

In one particular example a process for converting a complex bio-oil containing cyclic compounds into desired higher molecular weight materials includes reacting a precursor containing cyclic compounds in a first a reactor with a ring-contraction catalyst having 1% Pt/HZSM-22;to selectively produce C-5 ring containing compounds; and then reacting the C-5 ring containing compounds with a C-5 ring opening catalyst metal catalyst comprising 1% Ir/Al2O3, in a second reactor to yield a high molecular weight material. The first reactor operates under a first set of operating conditions and the second reactor operates under a second set of conditions. The first and second sets of conditions are different.

In one particular example, a process for converting a complex bio-oil containing cyclic compounds into desired higher molecular weight materials includes reacting a precursor containing cyclic compounds in a first a reactor with a controlled ring-opening catalyst having 1% Pt/HZSM-22; to selectively convert multi-rings products into desired branched C-6 ring containing compounds; and then reacting the C-5 ring containing compounds with a C5 ring opening catalyst metal catalyst comprising 1% Ir/Al2O3, in a second reactor to yield a higher molecular weight material. The first reactor operates under a first set of operating conditions and the second reactor operates under a second set of conditions. The first and second sets of conditions are different.

A system for converting bio-oils containing cyclic compounds or biologically-derived cyclics compounds into high molecular weight materials made up of a first reactor containing a ring contraction catalyst, the first reactor configured to operate reacting a precursor containing cyclic compounds in a first a reactor with a ring-contraction catalyst to selectively produce C5 ring containing compounds; and a second reactor containing a C5 ring opening catalyst in a second reactor to yield a high molecular weight material. The first and second reactors connected to devices that enable the operating conditions of the first and second reactors to be different.

Various advantages and novel features of the present disclosure are described herein and will become further readily apparent to those skilled in this art from the following detailed description. In the preceding and following descriptions I have shown and described only the preferred embodiment of the disclosure, by way of illustration of the best mode contemplated for carrying out the disclosure. As will be realized, the disclosure is capable of modification in various respects without departing from the disclosure. Accordingly, the drawings and description of the preferred embodiment set forth hereafter are to be regarded as illustrative in nature, and not as restrictive.

BRIEF DESCRIPTION OF THE DRAWINGS

FIG. 2 is a process diagram of the preferred embodiment of the present disclosure.

DETAILED DESCRIPTION OF THE DISCLOSURE

Figure 1:
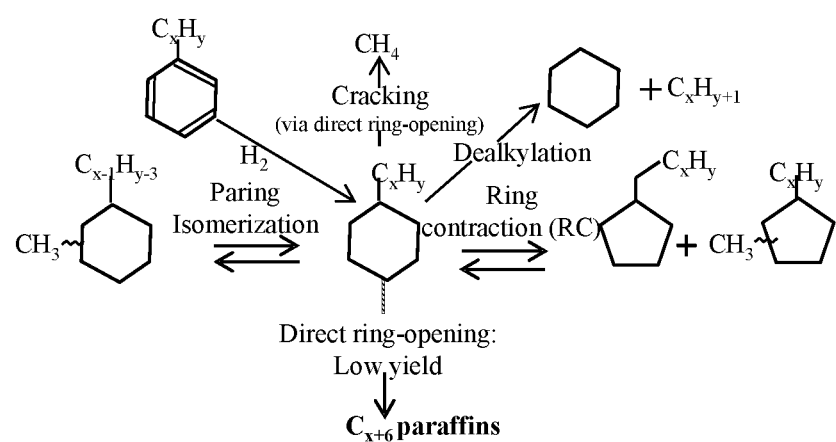
FIG. 1 is view of a reactions described in the present application

The following description includes a preferred mode of one embodiment of the invention. It will be clear from this disclosure that the invention is not limited to these illustrated embodiments but that a variety of modifications and embodiments are also envisioned. Therefore the present description should be seen as illustrative and not limiting. While the disclosure is susceptible of various modifications and alternative constructions, it should be understood, that there is no intention to limit the disclosure to the specific form disclosed, but, on the contrary, the disclosure is to cover all modifications, alternative constructions, and equivalents falling within the spirit and scope of the disclosure as defined in the claims.

As described above, a variety of technologies and methods have been attempted to try and prepare, upgrade or otherwise modify complex bio-oils so as to enable their use as a starting material or replacement for fossil fuel based crude oil in standard fossil fuel refining and transportation processes and infrastructure. The present disclosure provides a significant advance in this regard by providing a methodology for converting these problematic cyclic compounds found in bio-oils into acyclic paraffins. To the best of our knowledge however, there has been no other group that have been able to convert these cyclic compounds within a bio-oil arrangement successfully.

Conventionally, ring-opening processes are conducted over solid acid catalysts (carbocation route) or over metals (hydrogenolysis route) or over bifunctional catalysts containing a metal and an acid function. This carbocation route typically leads to unacceptable low yields of desired high molecular weight paraffins with dealkylation and/or cracking leading to undesired products. Hydrogenolysis for C6-ring containing compounds which make up a predominant portion of (partially) hydrotreated bio-oils, such as methylcyclohexane has been a difficult problem to solve.

As illustrated in FIG. 1, during ring opening of substituted C6-rings, several reactions can take place at the same time leading to many products. Ideally the C6-ring is first contracted to a C5-ring and then the C5-ring is opened to form n- and iso-paraffins. Up to now however, research work conducted to favor this pathway has not been very successful. When metal and acid are mixed together, multiple reactions take place simultaneously leading to a series of unresolved problems.

In the present methodology, as shown in FIG. 2 we separate the acid and metal functions into two catalysts loaded in two separate reactors. Since ring contraction and ring opening present different kinetics, efficiency was improved with a system consisting of two reactors instead of one. Hence, we have developed a novel two-step process of treating a complex bio-oil by passing that complex bio-oil through a reactor with a "ring contraction catalyst" to selectively form C5-ring containing compounds and then passing the mixture containing these C5-ring containing compounds through a second reactor containing a "C5 ring opening catalyst" to maximize the yield of high molecular weight paraffins and minimize carbon loss via cracking reactions.

In one arrangement this two-step process was used to open a mixture of aromatics and naphthenic $C_{6+}$ ring containing compounds (e.g. propyl benzene, methylcyclohexane, methylcyclohexanol). The ring opening was accomplished in two separate steps in such a way that both steps can be optimized by operation under different process conditions (i.e. different pressure, temperature and throughput) to maximize the formation of high molecular weight paraffins and minimize carbon loss. In this process a first reactor loaded with Pt and/or Pd catalysts contained an acid catalyst to convert the $C_6$ ring containing compounds into $C_5$ ring containing compounds; a ring contraction step. A second reactor contained a metal catalyst such as $Ir/Al_2O_3$ to convert the $C_5$ ring containing compounds into paraffins which were determined to be highly valuable for diesel and jet markets; a $C_5$-ring opening step. This pathway was successfully demonstrated with model compounds and real bio-oils.

In a first set of experiments methylcyclohexane was used as model naphthenic compound. For the two-step process, the ring-contraction step is conducted with a first reactor loaded with a 1 wt % Pt/HZSM-22 catalyst while operating under mild conditions (320° C., 20 bars). The ring-contraction product is then fed to a second reactor loaded with a 1 wt % $Ir/Al_2O_3$ catalyst and operating at 280° C. and 20 bars. For this novel two-step process, 49% yield toward $C_7$ paraffins (see Table 1) is obtained. The efficiency of the two-step process was compared to a one step process. For the one-step process different configurations were tested where the reactor was loaded with either a 1 wt % Pt/HZSM-5 (acid catalyst-carbocation route) or 1 wt % $Ir/Al_2O_3$ (metal catalyst-hydrogenolysis route) or a 1 wt % Pt/HZSM-22 and 1 wt% $Ir/Al_2O_3$ mixed together or a 1 wt % Pt/HZSM-22 on top of a 1 wt % $Ir/Al_2O_3$ catalyst. Considering the one-step process with a 1 wt % Pt/HZSM-5 catalyst, only 3.1% yield of $C_7$ paraffins is obtained due to extensive cracking. When operating with a 1 wt % $Ir/Al_2O_3$ catalyst only 26.5% yield of $C_7$ paraffins was obtained due again to significant cracking. For a one-step process where 1 wt % Pt/HZSM-22 and 1 wt % $Ir/Al_2O_3$ were mixed together and loaded in one reactor, the yield toward the $C_7$ paraffins is equal to 28.5%. Comparatively, when the 1 wt % Pt/HZSM-22 is located on top of the 1 wt % $Ir/Al_2O_3$ catalyst the yield toward the $C_7$ paraffins is higher and equal to 45.6%. The ring contraction followed by the ring opening was found to be key in avoiding undesirable cracking reactions. The 2-step process offers advantages compared to a one-step process where the 1 wt % Pt/HZSM-22 is located on top of the 1 wt % $Ir/Al_2O_3$ catalyst since not only higher yield toward $C_7$ paraffins is obtained but also less cyclics and less $C_1$-$C_4$ cracking products are formed.

TABLE 1

| Process | Catalyst | Yield (%) | | | | |
|---|---|---|---|---|---|---|
| (% denotes wt %) | (% denotes wt %) | $C_1$-$C_4$ paraffins | $C_5$-$C_6$ paraffins | $C_7$ paraffins | $C_6$-$C_7$ cyclic paraffins | Toluene |
| one-step carbocation route | 1% Pt/HZSM5 | 74.8 | 5.8 | 3.1 | 10.5 | 0.8 |
| one-step Hydrogenolysis route | 1% Ir/Al$_2$O$_3$ | 25.0 | 47.5 | 26.5 | 1 | 0 |
| one-step step with mixed catalysts in one reactor | 1% Pt/HZSM22 + 1% Ir/Al$_2$O$_3$ | 29.1 | 29.8 | 28.5 | 12.6 | 0 |
| one-step with 1% Pt/ZSM22 on top of 1% Ir/Al$_2$O$_3$ in one reactor | 1% Pt/HZSM22 + 1% Ir/Al$_2$O$_3$ | 16.2 | 11.0 | 45.6 | 23.0 | 0.0 |
| 2-step process* (2 reactors in series) | 1% Pt/HZSM22 + 1% Ir/Al$_2$O$_3$* | 11.3 | 17.6 | 49.0 | 16.7 | 0.9 |

T = 320° C., P = 300 psig, H$_2$: methylcyclohexane = 10 (molar), space velocity varied to ensure conversion >95%.
*for the two-step process the second reactor is operated at 280° C.

Proof of concept was also demonstrated with model compounds found in hydrothermal liquefaction bio-oils. Table 2 presents the composition of the liquid hydrocarbons feed and product obtained after ring-contraction step in a mixture of model compounds found in hydrothermal liquefaction bio-oil. The aromatics (e.g. phenanthrene, pyrene) are fully converted into cyclohexanes and cyclopentanes demonstrating that this technology can be applied to multi-rings/aromatics compounds found in HTL bio-oils.

TABLE 2

| | GC-MS mass % | |
|---|---|---|
| Compounds | Feed | Product |
| $C_3$-$C_5$ (iso)paraffins | — | 6.7 |
| $C_6$-$C_7$ (iso)paraffins | 45.5 | 48.4 |
| $C_8^+$ (iso)paraffins | 12.9 | 2.8 |
| Branched cyclopentanes | — | 18.5 |
| Branched cyclohexanes | — | 17.3 |
| Aromatics* | 38.5 | — |
| Oxygenated compounds | 3.4 | 0.8 |
| Other cyclic compounds | — | 3.8 |

T = 280° C., P = 320 psig, LHSV = 0.9 hr$^{-1}$, H$_2$(95%/N$_2$) = 120 sccm, catalyst = 1% Pt/HY(720).
*Aromatics consist of phenanthrene, pyrene, propylbenzene, 2-methyl-naphthalene, dimethyl-naphthalene.

We have also investigated an extension of the 2-step process for biologically-derived compounds, namely caryophyllene and patchoulol that are both multi-rings compounds. Caryophyllene is liquid at room temperature and hence was processed neat. Patchoulol is a solid and was thus dissolved in isooctane at 30 wt % to facilitate processing. Table 3 presents the composition of the product when both compounds were processed. Complete conversion of the starting multi-ring structures was observed. $C_6$ ring structures abound on the treated products and results from the ring-contraction. A substantial portion of the product did convert to isoparaffins and olefins via ring-opening.

| Feed Products | caryophyllene GC-MS mass % | Patchoulol GC-MS mass % |
|---|---|---|
| $C_3$-$C_5$ paraffins | 5.1 | — |
| $C_6$-$C_7$ (iso)paraffins | 11.7 | 16.4 |
| $C_8^+$ (iso)paraffins | 13.6 | — |
| $C_3$-$C_7$ olefins | 2.0 | 5.9 |
| $C_8^+$ olefins | 4.9 | 14.3 |
| Cyclics $C_5$ | 8.9 | 2.3 |
| Cyclics $C_6$ | 46.3 | 21.5 |
| Naphthalene type molecules | 1.4 | 0.5 |
| Adamantane | 0.4 | 4.7 |
| Oxygenates | 4.2 | 7.3 |
| organics | 1.0 | 0.8 |
| Cyclics $C_8$ | — | 0.4 |
| bycyclics | — | 0.6 |

For the ring contraction step: catalyst is 1% Pt/HY(901), T = 320° C., P = 300 psig, LHSV = 0.9-0.11 hr$^{-1}$.
For the ring-opening step: catalyst is 1% Ir/Al$_2$O$_3$, T = 280° C., P = 300 psig, LHSV = 0.8 hr$^{-1}$.

In a second set of experiments a two-step process was then applied to real bio-oils. The gasoline fraction of a hydrotreated fast-pyrolysis oil (pine wood) was used as feedstock. As shown in Table 4 the feedstock contains mainly aromatics (31%), branched cyclohexanes (21%) and branched cyclopentanes (15%). The ring opening product contains mainly (iso) paraffins/olefins (56%) and cyclohexanes (28%). These results indicate that the aromatics (single or multi-rings compounds) were fully converted into branched cyclohexanes and a fraction of the branched cyclohexanes was either converted into cyclopentanes or (iso) paraffins and olefins. The cyclopentanes product from the first reactor/step were converted into (iso)paraffins and olefins in the second reactor step.

TABLE 4

| | GC-MS (mass %) | |
|---|---|---|
| Compounds | Feed | Product |
| $C_3$-$C_5$ (iso)paraffins/olefins | 2.4 | 3.2 |
| $C_6$-$C_7$ (iso)paraffins/olefins | 6.7 | 28.9 |
| $C_8^+$ (iso)paraffins/olefins | 13.1 | 24.1 |
| Branched cyclopentanes | 15.3 | 11.1 |
| Branched cyclohexanes | 21.3 | 28.4 |
| Aromatics | 31.1 | — |
| Oxygenated compounds | 5.8 | 1.3 |
| Other cyclic compounds | 4.3 | 2.4 |

Reaction conditions for the ring-contraction step: T = 320° C., P = 300 psig, H$_2$ (95%/N$_2$) = 36 sccm, LHSV = 0.16 hr$^{-1}$, catalyst is 1% Pt/HZSM-22.
Reaction conditions for the ring-opening step: T = 320° C., P = 300 psig, H$_2$ (95%/N$_2$) = 36 sccm, LHSV = 0.3 hr$^{-1}$, catalyst is 1% Ir/Al$_2$O$_3$.

Another set of experiments using a diesel fraction of a hydrotreated fast-pyrolysis oil (oak wood) were also conducted. Composition of the feed and the ring opening product are presented in Table 3. As seen in Table 5, the feed contains mainly aromatics (39.8%), organic and oxygenated cyclic compounds (37.1%) that are converted predominantly into branched cyclohexanes (45.6%) and C8+ (iso) parrafins (31.9%).

TABLE 5

| | GC-MS (mass %) | |
|---|---|---|
| Compounds | Feed | Product |
| $C_3$-$C_5$ (iso)paraffins | — | 2.9 |
| $C_6$-$C_7$ (iso)paraffins | — | 9.3 |
| $C_8^+$ (iso)paraffins | 6.6 | 31.9 |
| Branched cyclopentanes | 1.5 | 6.5 |

TABLE 5-continued

| | GC-MS (mass %) | |
|---|---|---|
| Compounds | Feed | Product |
| Branched cyclohexanes | 8.1 | 45.6 |
| Aromatics* | 39.8 | 1.1 |
| Organic and Oxygenated compounds** | 37.1 | 1.2 |
| Others | 6.9 | 1.5 |

Reaction conditions for the ring-contraction step: T = 300° C., P = 300 psig, $H_2$ (95%/$N_2$) = 32 sccm, LHSV = 0.03 $hr^{-1}$, catalyst is 1% Pt/HY(901).
Reaction conditions for the ring-opening step: T = 280° C., P = 300 psig, $H_2$ (95%/$N_2$) = 32 sccm, LHSV = 0.15 $hr^{-1}$, catalyst is 1% Ir/$Al_2O_3$.
*e.g. ethyl-tetrahydro-naphthalene
**mainly cyclic oxygenates compounds such as phenolics.

As described above, ring opening of hydroprocessed bio-oils is feasible using our inventive two-step process. Most of the research in the current art has been conducted for the ring opening of cyclic compounds in one step using one bifunctional catalyst composed of a metal and an acid functions. However, cracking and dealkylation are major issues leading to carbon loss and undesired products such as methane. In the present invention, we have loaded a ring contraction catalyst and a -ring opening catalyst into two separate reactors. The advantage of this two-step process is that both steps can be operated under different process conditions (i.e. different pressure, temperature and throughput). Since the ring contraction step and the ring opening step present different kinetics, the efficiency is thus improved, the formation of desired high molecular weight paraffins is maximized and carbon loss (i.e. cracking) is minimized. This presents significant advantages over the prior art in that it provides a selective ring opening processes for converting aromatics and naphthenic ring-containing compounds into high molecular weight paraffins with minimal carbon loss. This process could then find industrial application in upgrading of (partially) hydroprocessed bio-oils, and upgrading of any bio-oil or petroleum fuel containing cyclic compounds. Thus providing a substantial step forward in moving bio-oils toward becoming a replacement for fossil crude oil in transportation applications.

While various preferred embodiments of the disclosure are shown and described, it is to be distinctly understood that this disclosure is not limited thereto but may be variously embodied to practice within the scope of the following claims. From the foregoing description, it will be apparent that various changes may be made without departing from the spirit and scope of the disclosure as defined by the following claims.

What is claimed is:

1. A process for converting cyclic compounds having at least six carbons, the process comprising the steps of:
   providing a bio-oil feedstock containing C-6 or greater cyclic compounds, the bio-oil feedstock having complex microemulsions of aqueous and non-aqueous phases containing different organic and inorganic compounds including esters, acids, aldehydes, alcohols, ketones, sugars, and various phenol derivatives;
   reacting the bio-oil feedstock containing C-6 or greater cyclic compounds in a first reactor with an acidic ring-contraction catalyst containing at least one metal to open and reduce the C-6 or greater cyclic compounds and selectively produce C-5 ring containing compounds from the C-6 or greater cyclic compounds; and
   reacting the C-5 ring containing compounds with a C-5 ring opening catalyst in a second reactor to yield a higher molecular weight material comprising paraffins,
   wherein the step of reacting the bio-oil feedstock occurs under a first set of operating conditions comprising a temperature 320° C. and a pressure 20 bars and the step of reacting the C-5 ring containing compounds operates under a second set of conditions comprising a temperature 280° C. and a pressure 20 bars.

2. The process of claim 1 wherein the first reactor is loaded with the acidic ring-contraction catalyst and operates at a temperature 320° C. and a pressure 20 bars and the second reactor is loaded with the C-5 ring opening catalyst and operates at a temperature 280° C. and a pressure 20 bars.

3. The process of claim 1 wherein the acidic ring-contraction catalyst in the first reactor is an acid catalyst containing Pt.

4. The process of claim 1 wherein the acidic ring-contraction catalyst in the first reactor is an acid catalyst containing Pd.

5. The process of claim 1 wherein the C-5 ring opening catalyst in the second reactor is a metal catalyst.

6. The process of claim 5 wherein the C-5 ring opening catalyst comprises Ir.

7. The process of claim 1 wherein the higher molecular weight material is paraffins.

8. A process for converting cyclic compounds from a bio-oil feedstock into higher molecular weight materials comprising paraffins, the process comprising the steps of:
   providing a bio-oil feedstock containing C-6 or greater cyclic compounds, the bio-oil feedstock having complex microemulsions of aqueous and non-aqueous phases containing different organic and inorganic compounds including esters, acids, aldehydes, alcohols, ketones, sugars, and various phenol derivatives;
   reacting the bio-oil feedstock containing C-6 or greater cyclic compounds in a first a reactor with a ring-contraction catalyst comprising 1 wt % Pt/HZSM-22 thereby selectively producing $C_5$ ring containing compounds; and
   reacting the $C_5$ ring containing compounds with a $C_5$ ring opening metal catalyst comprising 1 wt % Ir/$Al_2O_3$ in a second reactor to yield a higher molecular weight material comprising paraffins,
   wherein the first reactor operates at a temperature 320° C. and a pressure 20 bars and the second reactor operates at a temperature 280° C. and a pressure 20 bars.

9. The process of claim 8 wherein the higher molecular weight material is paraffins.

10. The process of claim 8 wherein the ring-contraction catalyst is 1 wt % Pt/HZSM-22.

11. The process of claim 8 wherein the $C_5$ ring opening metal catalyst is 1 wt % Ir/$Al_2O_3$.

* * * * *